(12) United States Patent
Greenberg et al.

(10) Patent No.: US 9,532,451 B2
(45) Date of Patent: Dec. 27, 2016

(54) BIOCOMPATIBLE BONDING METHOD AND ELECTRONICS PACKAGE SUITABLE FOR IMPLANTATION

(71) Applicant: SECOND SIGHT MEDICAL PRODUCTS, INC., Sylmar, CA (US)

(72) Inventors: Robert Greenberg, Los Angeles, CA (US); Neil Talbot, La Crescenta, CA (US); Jerry Ok, Canyon Country, CA (US); Jordan Neysmith, Pasadena, CA (US); David Zhou, Saugus, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 0 days.

(21) Appl. No.: 14/987,574

(22) Filed: Jan. 4, 2016

(65) Prior Publication Data

US 2016/0255720 A1    Sep. 1, 2016

Related U.S. Application Data

(62) Division of application No. 14/516,476, filed on Oct. 16, 2014, now Pat. No. 9,258,902, which is a division
(Continued)

(51) Int. Cl.
| | |
|---|---|
| A61N 1/36 | (2006.01) |
| A61N 1/375 | (2006.01) |
| H05K 1/11 | (2006.01) |
| H05K 1/09 | (2006.01) |
| H05K 1/02 | (2006.01) |

(Continued)

(52) U.S. Cl.
CPC ............ *H05K 1/113* (2013.01); *A61N 1/0543* (2013.01); *A61N 1/36046* (2013.01); *A61N 1/3758* (2013.01); *H05K 1/028* (2013.01); *H05K 1/09* (2013.01); *H05K 3/4038* (2013.01); *H05K 3/4084* (2013.01); *H05K 2203/0733* (2013.01)

(58) Field of Classification Search
None
See application file for complete search history.

(56) References Cited

U.S. PATENT DOCUMENTS

| | | |
|---|---|---|
| 3,699,970 A | 10/1972 | Brindley |
| 4,573,481 A | 3/1986 | Bullara |
| (Continued) | | |

OTHER PUBLICATIONS

Hansjoerg Beutel, Thomas Stieglitz, Joerg Uwe Meyer, "Versatile 'Microflex'-Based Interconnection Technique."
(Continued)

*Primary Examiner* — Brian T Gedeon
(74) *Attorney, Agent, or Firm* — Scott B. Dunbar

(57) ABSTRACT

The invention is directed to a method of bonding a hermetically sealed electronics package to an electrode or a flexible circuit and the resulting electronics package, that is suitable for implantation in living tissue, such as for a retinal or cortical electrode array to enable restoration of sight to certain non-sighted individuals. The hermetically sealed electronics package is directly bonded to the flex circuit or electrode by electroplating a biocompatible material, such as platinum or gold, effectively forming a studbump connection, which bonds the flex circuit to the electronics package. The resulting electronic device is biocompatible and is suitable for long-term implantation in living tissue.

11 Claims, 16 Drawing Sheets

Related U.S. Application Data of application No. 13/009,769, filed on Jan. 19, 2011, now Pat. No. 8,880,165, which is a division of application No. 11/517,860, filed on Sep. 7, 2006, now Pat. No. 7,904,148, which is a division of application No. 10/236,396, filed on Sep. 6, 2002, now Pat. No. 7,142,909, which is a division of application No. 10/174,349, filed on Jun. 17, 2002, now Pat. No. 7,211,103.

(51) Int. Cl.
*H05K 3/40* (2006.01)
*A61N 1/05* (2006.01)

(56) References Cited

U.S. PATENT DOCUMENTS

| | | | |
|---|---|---|---|
| 4,837,049 A | 6/1989 | Byers | |
| 5,109,844 A | 5/1992 | de Juan | |
| 5,215,088 A | 6/1993 | Normann | |
| 5,935,155 A | 8/1999 | Humayun | |
| 6,400,989 B1 | 6/2002 | Eckmiller | |
| 6,458,157 B1 | 10/2002 | Suaning | |
| 2005/0110163 A1* | 5/2005 | Koo | H01L 21/563 257/778 |
| 2015/0194409 A1* | 7/2015 | Chuang | H01L 25/0657 257/737 |

OTHER PUBLICATIONS

Proc. SPIE Conf on Smart Electronics and MEMS, San Diego, Cal., Mar. 1998, vol. 3328, pp. 174-182.

L. Del Castillo, R. Graber, S. D'Agostino, M. Mojarradi and A. Mottiwala, "Flip Chip Packaging of a MEMS Neuro-Prosthetic System."

Proc. IMAPS International Conference & Exhibition on Advanced Packaging and Systems, Reno, Nevada, Mar. 2002, pp. 158-163.

M. Pourbaix, Atlas of Electrochemical Equilibria in Aqueous Solutions, National Association of Corrosion Engineers, Houston, 1974, pp. 399-405.

Joseph V. Mantese and William V. Alcini, "Platinum Wire Wedge Bonding: A New IC and Microsensor Interconnect," J. Electronic Materials, 17 (4) 1988, pp. 285-289.

Andreas Schneider, Thomas Stieglitz, Werner Haberer, Hansjörg Beutel, and J.-Uwe Meyer.

Flexible Interconnects for Biomedical Microsystems Assembly, IMAPS Conference, Jan. 31, 2001.

Materials Engineering, Materials Selector 1990, Penton Publishing, 1989, p. 122.

\* cited by examiner

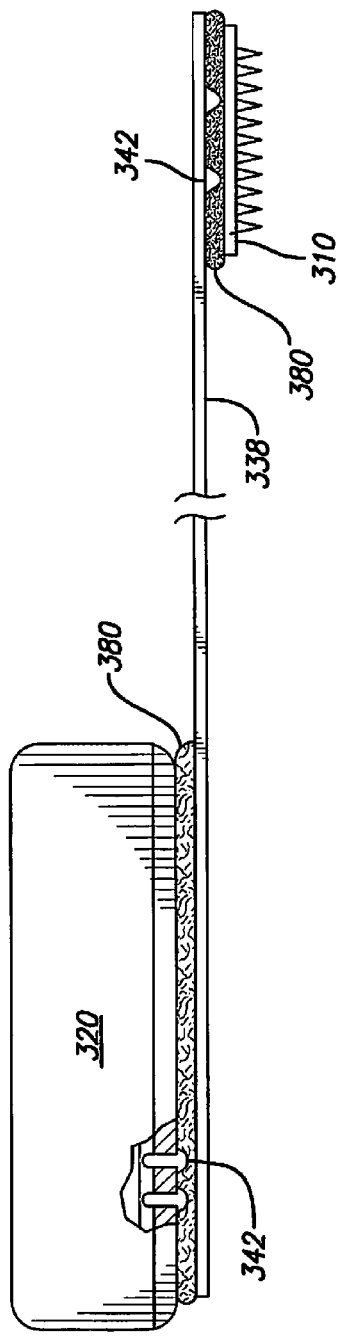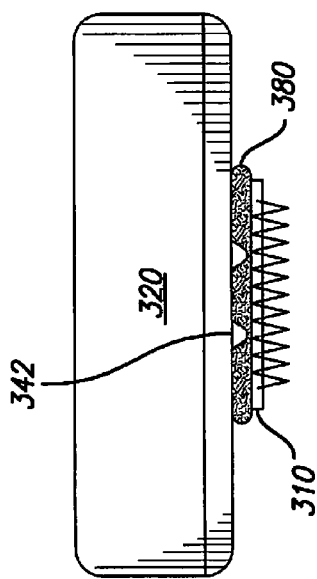

US 9,532,451 B2

BIOCOMPATIBLE BONDING METHOD AND ELECTRONICS PACKAGE SUITABLE FOR IMPLANTATION

CROSS REFERENCE TO RELATED APPLICATIONS

This patent application is a divisional application of U.S. patent application Ser. No. 14/516,476, filed Oct. 16, 2014, entitled Biocompatible Bonding Method and Electronics Package Suitable for Implantation, now U.S. Pat. No. 9,258,902, which is a divisional application of U.S. patent application Ser. No. 13/009,769, filed Jan. 19, 2011, entitled Biocompatible Bonding Method and Electronics Package Suitable for Implantation, now U.S. Pat. No. 8,880,165, which is a divisional application of U.S. patent application Ser. No. 11/517,860, filed Sep. 7, 2006, entitled Biocompatible Bonding Method and Electronics Package Suitable for Implantation, now U.S. Pat. No. 7,904,148, which is a divisional application of U.S. patent application Ser. No. 10/236,396, filed Sep. 6, 2002, entitled Biocompatible Bonding Method and Electronics Package Suitable for Implantation, now U.S. Pat. No. 7,142,909, the disclosure of which is incorporated herein by reference and which is a continuation-in-part of U.S. patent application Ser. No. 10/174,349, filed on Jun. 17, 2002, entitled Biocompatible Bonding Method and Electronics Package Suitable for Implantation, now U.S. Pat. No. 7,211,103, the disclosure of which is incorporated herein by reference.

The application claims benefit of U.S. patent application Ser. No. 10/226,976, filed on Aug. 23, 2002, now U.S. Pat. No. 6,794,533, entitled Platinum Electrode and Method for Manufacturing the Same, the disclosure of which is incorporated herein by reference, and which claims benefit of U.S. Provisional Application No. 60/372,062, filed on Apr. 11, 2002, entitled Platinum Deposition for Electrodes, the disclosure of which is incorporated herein by reference.

GOVERNMENT RIGHTS NOTICE

This invention was made with government support under grant No. R24EY12893-01. The government has certain rights in the invention.

FIELD OF THE INVENTION

This invention relates to an electrode array or flexible circuit, electronics package and a method of bonding a flexible circuit or electrode array to an integrated circuit or electronics package.

BACKGROUND OF THE INVENTION

Arrays of electrodes for neural stimulation are commonly used for a variety of purposes. Some examples include U.S. Pat. No. 3,699,970 to Brindley, which describes an array of cortical electrodes for visual stimulation. Each electrode is attached to a separate inductive coil for signal and power. U.S. Pat. No. 4,573,481 to Bullara describes a helical electrode to be wrapped around an individual nerve fiber. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. U.S. Pat. No. 5,109,844 to de Juan describes a flat electrode array placed against the retina for visual stimulation. U.S. Pat. No. 5,935,155 to Humayun describes a retinal prosthesis for use with a flat retinal array.

Packaging of a biomedical device intended for implantation in the eye, and more specifically for physical contact with the retina, presents a unique interconnection challenge. The consistency of the retina is comparable to that of wet tissue paper and the biological media inside the eye is a corrosive saline liquid environment.

Thus, the device to be placed against the retina, in addition to being comprised of biocompatible, electrochemically stable materials, must appropriately conform to the curvature of the eye, being sufficiently flexible and gentle in contact with the retina to avoid tissue damage, as discussed in Andreas Schneider, Thomas Stieglitz, Werner Haberer, Hansjorg Beutel, and J.-Uwe Meyer, "Flexible Interconnects for Biomedical Microsystems Assembly, IMAPS Conference, Jan. 31, 2001. It is also desirable that this device, an electrode array, provides a maximum density of stimulation electrodes. A commonly accepted design for an electrode array is a very thin, flexible conductor cable. It is possible to fabricate a suitable electrode array using discrete wires, but with this approach, a high number of stimulation electrodes cannot be achieved without sacrificing cable flexibility (to a maximum of about 16 electrodes).

A lithographically fabricated thin film flex circuit electrode array overcomes such limitations. A thin film flex circuit electrode array can be made as thin as 10 um (0.0004 inches) while accommodating about 60 electrodes in a single circuit routing layer. The flex circuit electrode array is essentially a passive conductor ribbon that is an array of electrode pads, on one end, that contact the retina and on the other end an array of bond pads that must individually mate electrically and mechanically to the electrical contacts of a hermetically sealed electronics package. These contacts may emerge on the outside of the hermetic package as an array of protruding pins or as vias flush to a package surface. A suitable interconnection method must not only serve as the interface between the two components, but must also provide electrical insulation between neighboring pathways and mechanical fastening between the two components.

Many methods exist in the electronics industry for attaching an integrated circuit to a flexible circuit. Commonly used methods include wirebonding, anisotropic-conductive films, and "flip-chip" bumping. However, none of these methods results in a biocompatible connection. Common materials used in these connections are tin-lead solder, indium and gold. Each of these materials has limitations on its use as an implant. Lead is a known neurotoxin. Indium corrodes when placed in a saline environment. Gold, although relatively inert and biocompatible, migrates in a saline solution, when electric current is passed through it, resulting in unreliable connections.

In many implantable devices, the package contacts are feedthrough pins to which discrete wires are welded and subsequently encapsulated with polymer materials. Such is the case in heart pacemaker and cochlear implant devices. Flexible circuits are not commonly used, if at all, as external components of proven implant designs. The inventor is unaware of prior art describing the welding of contacts to flex circuits.

Attachment by gold ball bumping has been demonstrated by the Fraunhofer group (see Hansjoerg Beutel, Thomas Stieglitz, Joerg Uwe Meyer, "Versatile 'Microflex'-Based Interconnection Technique," Proc. SPIE Conf on Smart Electronics and MEMS, San Diego, Calif., March 1998, vol 3328, pp 174-82) to rivet a flex circuit onto an integrated circuit. A robust bond can be achieved in this way. However, encapsulation proves difficult to effectively implement with this method. Because the gap between the chip and the flex circuit is not uniform, under fill with epoxy is not practical. Thus, electrical insulation cannot be achieved with conventional under fill technology. Further, as briefly discussed earlier, gold, while biocompatible, is not completely stable under the conditions present in an implant device since it "dissolves" by electromigration when implanted in living tissue and subject to an electric current (see M. Pourbaix, Atlas of Electrochemical Equilibria in Aqueous Solutions, National Association of Corrosion Engineers, Houston, 1974, pp 399-405).

Widespread use of flexible circuits can be found in high volume consumer electronics and automotive applications, such as stereos. These applications are not constrained by a biological environment. Component assembly onto flex circuits is commonly achieved by solder attachment. These flex circuits are also much more robust and bulkier than a typical implantable device. The standard flex circuit on the market is no less than 0.002 inches in total thickness. The trace metalization is etched copper foil, rather than thin film metal. Chip-scale package (CSP) assembly onto these flex circuits is done in ball-grid array (BGA) format, which uses solder balls attached to input-output contacts on the package base as the interconnect structures. The CSP is aligned to a corresponding metal pad array on the flex circuit and subjected to a solder reflow to create the interconnection. A metallurgical interconnect is achieved by solder wetting. The CSP assembly is then underfilled with an epoxy material to insulate the solder bumps and to provide a pre-load force from the shrinkage of the epoxy.

Direct chip attach methods are referred to as chip-on-flex (COF) and chip-on-board (COB). There have been some assemblies that utilize gold wirebonding to interconnect bare, integrated circuits to flexible circuits. The flipchip process is becoming a reliable interconnect method. Flipchip technology originates from IBM's Controlled Collapse Chip Connection (C4) process, which evolved to solder reflow technique. Flipchip enables minimization of the package footprint, saving valuable space on the circuit, since it does not require a fan out of wirebonds. While there are a variety of flipchip configurations available, solder ball attach is the most common method of forming an interconnect. A less developed approach to flipchip bonding is the use of conductive adhesive, such as epoxy or polyimide, bumps to replace solder balls. These bumps are typically silver-filled epoxy or polyimide, although electrically conductive particulate of select biocompatible metal, such as platinum, iridium, titanium, platinum alloys, iridium alloys, or titanium alloys in dust, flake, or powder form, may alternatively be used. This method does not achieve a metallurgical bond, but relies on adhesion. Polymer bump flip chip also requires underfill encapsulation. Conceivably, polymer bump attachment could be used on a chip scale package as well. COB flipchip attach can also be achieved by using gold stud bumps, as an alternative to solder balls. The gold bumps of the chip are bonded to gold contacts on the hard substrate by heat and pressure. A recent development in chip-to-package attachment was introduced by Intel Corporation as Bumpless Build Up Layer (BBUL) technology. In this approach, the package is grown (built up) around the die rather than assembling the die into a pre-made package. BBUL presents numerous advantages in reliability and performance over flipchip.

Known technologies for achieving a bond between a flexible circuit and a electronics package suffer from biocompatibility issues. Novel applications of a biomedical implant that utilize a flexible circuit attached to a rigid electronics package require excellent biocompatibility coupled with long term mechanical attachment stability, to assure long lived reliable electrical interconnection.

Known deposition techniques for a bond, such as an electrically conductive metal bond or "rivet" are limited to thin layers. Plating is one such known method that does not result in an acceptable bond. It is not known how to plate shiny platinum in layers greater than approximately 1 to 5 microns because the dense platinum layer peels off, probably due to internal stresses. Black platinum lacks the strength to be a good mechanical attachment, and also lack good electrical conductivity.

Known techniques for bonding an electronic package to a flex circuit do not result in a hermetic package that is suitable for implantation in living tissue. Therefore, it is desired to have a method of attaching a substrate to a flexible circuit that ensures that the bonded electronic package and flex circuit will function for long-term implant applications in living tissue.

SUMMARY OF THE INVENTION

An implantable electronic device comprising a hermetic electronics control unit, that is typically mounted on a substrate, that is bonded to a flexible circuit by an electroplated platinum or gold rivet-shaped connection. The resulting electronics assembly is biocompatible and long-lived when implanted in living tissue, such as in an eye or ear.

The novel features of the invention are set forth with particularity in the appended claims. The invention will be best understood from the following description when read in conjunction with the accompanying drawings.

OBJECTS OF THE INVENTION

It is an object of the invention to provide a hermetic, biocompatible electronics package that is attached to a flexible circuit.

It is an object of the invention to attach a hermetically sealed electronics package to a flexible circuit for implantation in living tissue.

It is an object of the invention to attach a hermetically sealed electronics package to a flexible circuit for implantation in living tissue to transmit electrical signals to living tissue, such as the retina.

It is an object of the invention to provide a hermetic, biocompatible electronics package that is attached directly to a substrate It is an object of the invention to provide a method of bonding a flexible circuit to a substrate with an electroplated rivet-shaped connection.

It is an object of the invention to provide a method of plating platinum as a rivet-shaped connection.

Other objects, advantages and novel features of the present invention will become apparent from the following detailed description of the invention when considered in conjunction with the accompanying drawing.

BRIEF DESCRIPTION OF THE DRAWINGS

FIG. 11 is a side view of a flexible circuit bonded to a rigid array.

FIG. 12 is a side view of an electronics control unit bonded to an array.

DETAILED DESCRIPTION OF THE PREFERRED EMBODIMENTS

The following description is the best mode presently contemplated for carrying out the invention. This description is not to be taken in a limiting sense, but is made merely for describing the general principles of the invention. The scope of the invention should be determined with reference to the claims.

Figure 1:
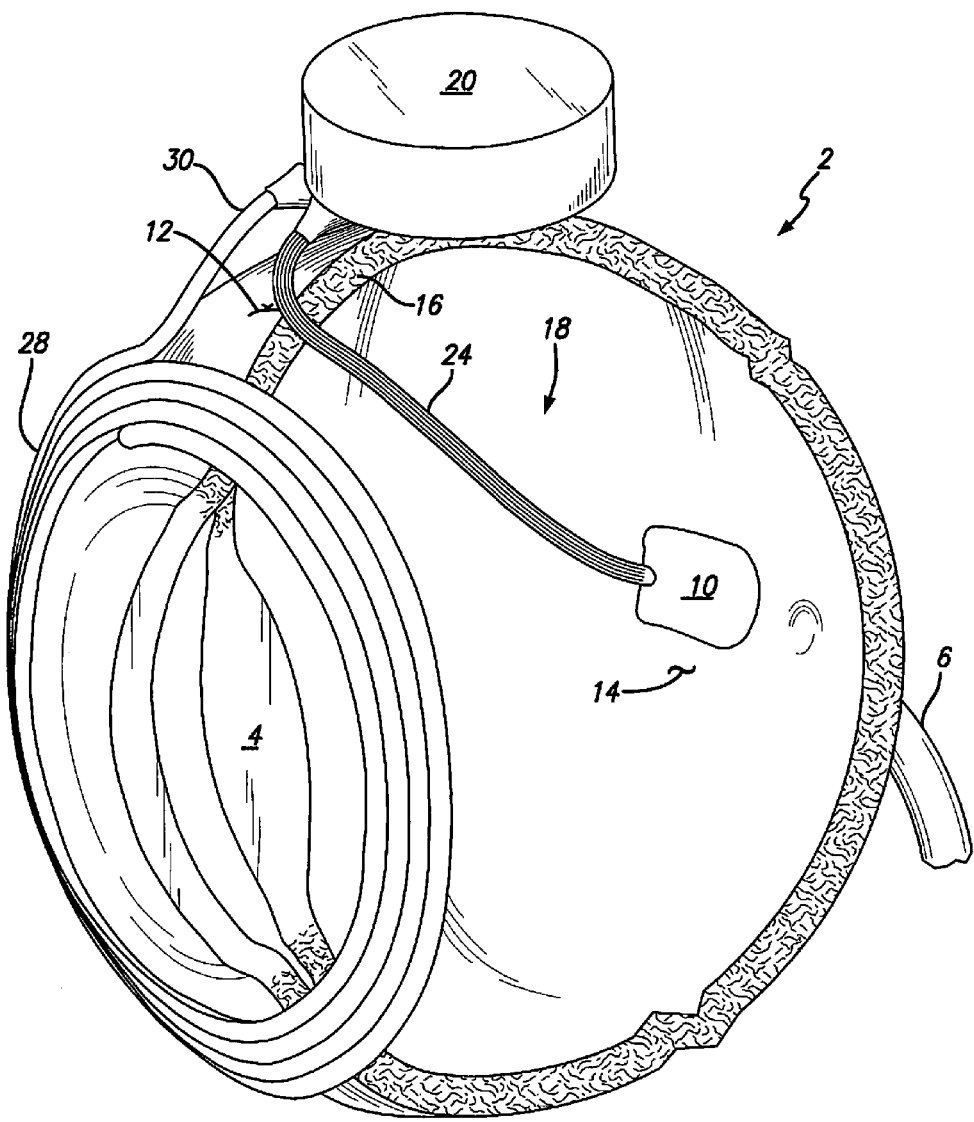
FIG. 1 illustrates a perspective cutaway view of an eye containing a flexible circuit electrode array.

The present invention provides a flexible circuit electronics package and a method of bonding a flexible circuit to a hermetic integrated circuit which is useful for a number of applications, including implantation in living tissue as a neural interface, such as a retinal electrode array or an electrical sensor. The tissue paper thin flexible circuit 18, FIG. 1, transmits electrical signals to the eye 2 by means of electrodes, that are located in a stimulating electrode array 10, that are in contact with the retina 14. It is obvious that in addition to a stimulating electrode array or sensing electrode, the electrodes may be contacts connecting to remote electrodes. FIG. 1 illustrates the electronics control unit 20 in a perspective cutaway view of an eye 2 containing a flexible circuit electrode array 18. The electronics control unit 20 is hermetically sealed. The electronics control unit 20 may be a hermetic ceramic case with electronics inside, or it may be a hermetically sealed integrated circuit, or any other environmentally sealed electronics package. The stimulating electrode array 10 is implanted on the retina 14. Flexible circuit ribbon 24 connects the stimulating electrode array 10 to the electronics control unit 20.

The flexible circuit ribbon 24 preferably passes through the sclera 16 of the eye 2 at incision 12. Another embodiment of the invention is the flexible circuit ribbon 24 replaced by alternative means of electrical interconnection, such as fine wires or thin cable. The lens 4 of the eye 2 is located opposite the retina 14. A coil 28, which detects electronic signals such as of images or to charge the electronics control unit 20 power supply, located outside the eye 2, near the lens 4, is connected to the electronics control unit 20 by wire 30.

Figure 2:
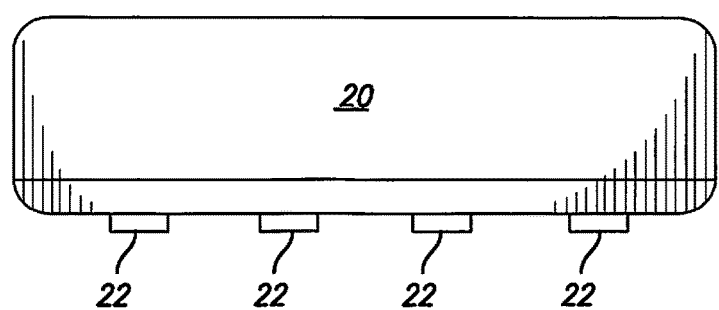
FIG. 2 is a side view of an electronics package.

FIG. 2 illustrates a side view of the hermetic electronics control unit 20 and the input/output contacts 22 that are located on the bottom of the unit 20. The input/output contacts 22 are bonded in the completed assembly to the flexible circuit 18. Thick film pad 23 is formed by known thick film technology, such as silk screening or plating.

Figure 3:
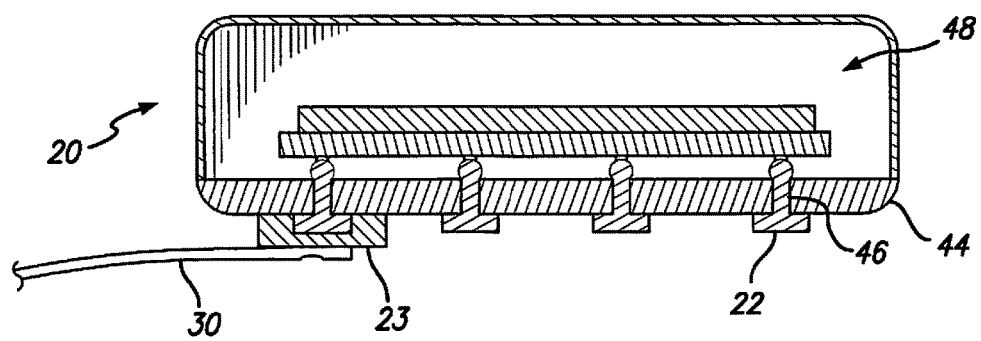
FIG. 3 illustrates a cutaway side view of an electronics package.

FIG. 3 illustrates a cutaway side view of the hermetic electronics control unit 20. The pad 23 facilitates attachment of wire 30, and is preferably comprised of a biocompatible material such as platinum, iridium, or alloys thereof, and is preferably comprised of platinum paste. Wire 30 is preferably bonded to pad 23 by welding. The microelectronics assembly 48 is mounted on the hybrid substrate 44. Vias 46 pass through the substrate 44 to input/output contacts 22. Electrical signals arrive by wire 30 and exit the electronics control unit 20 by input/output contacts 22.

Figure 4:
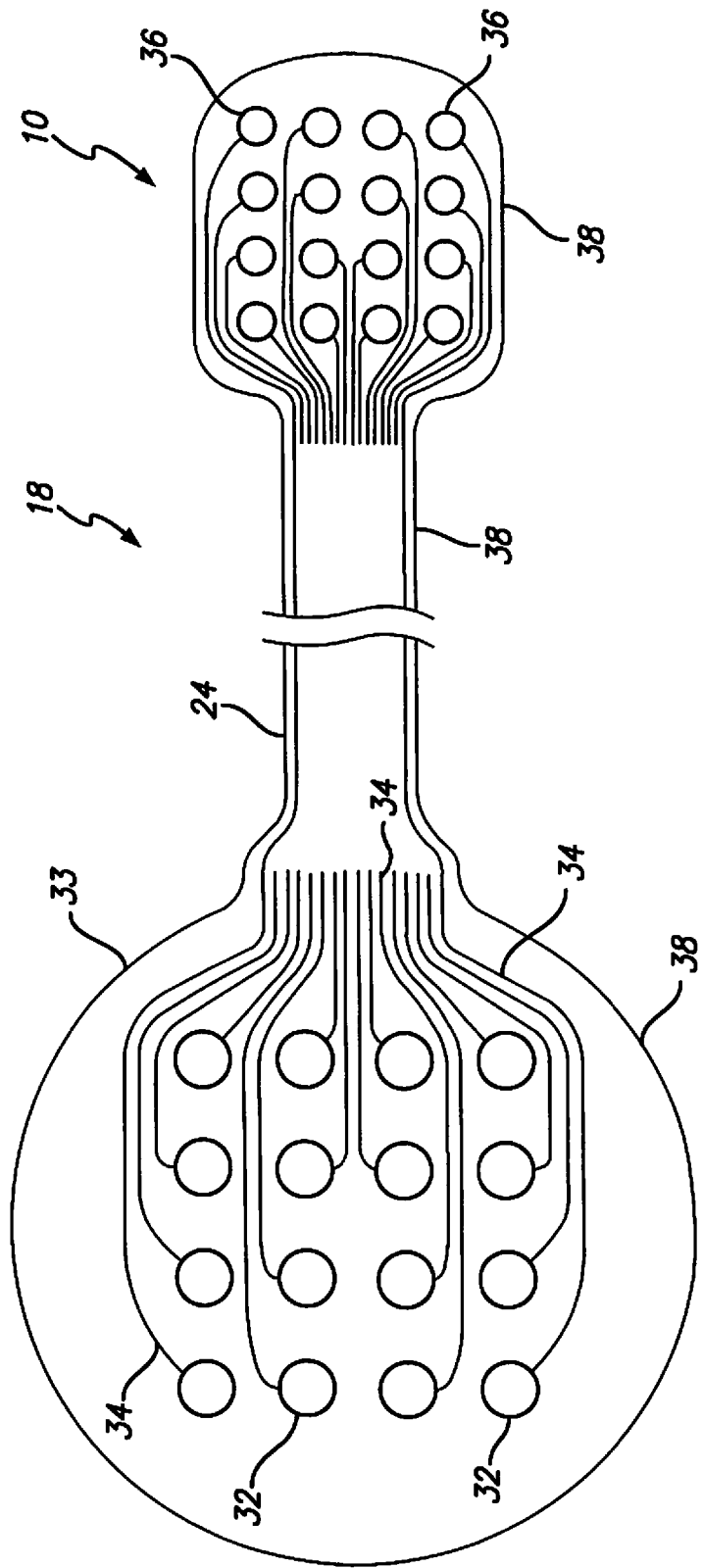
FIG. 4 is a top view of a flex circuit without the electronics package.

A top view of the flexible circuit 18 is illustrated in FIG. 4. Electrical signals from the electronics control unit 20 (see FIG. 3) pass into bond pads 32, which are mounted in bond pad end 33. Flexible electrically insulating substrate 38, is preferably comprised of polyimide. The signals pass from the bond pads 32 along traces 34, which pass along flexible circuit ribbon 24 to the stimulating electrode array 10. The array 10 contains the electrodes 36, which are implanted to make electrical contact with the retina 14 of the eye 2, illustrated in FIG. 1. An alternative bed of nails embodiment for the electrodes 36 is disclosed by Byers, et al. in U.S. Pat. No. 4,837,049.

Figure 5:
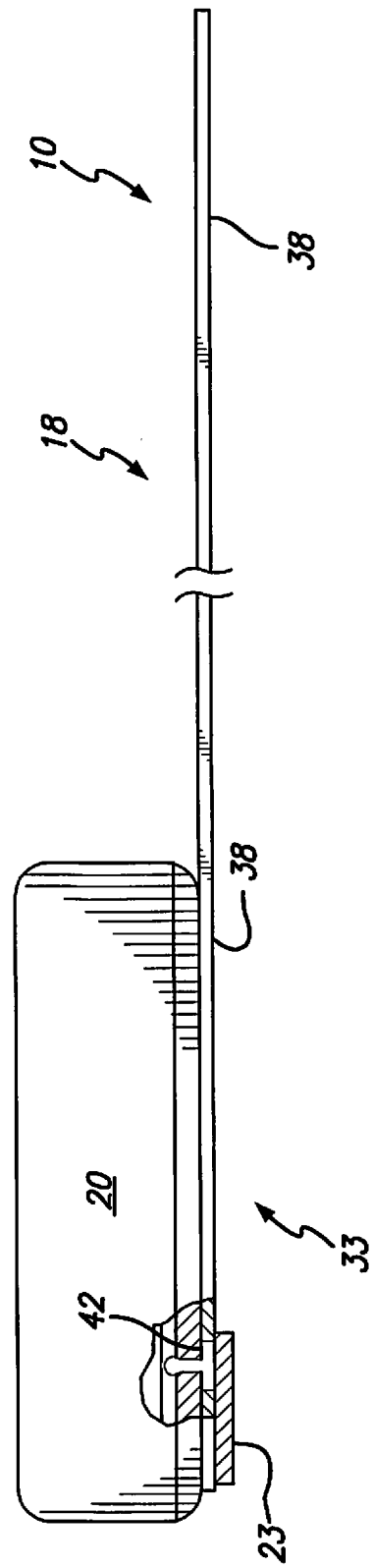
FIG. 5 presents a side view of a flex circuit with the electronics package.
Figure 6A:
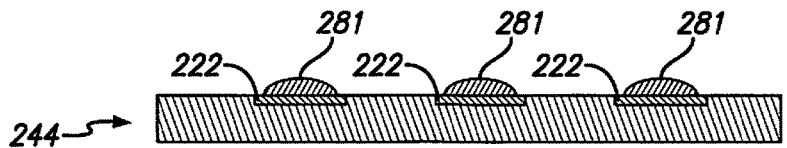
FIG. 6A depicts the beginning of the method of attaching a flexible circuit array to the electronics package where the substrate is prepared for bonding.
Figure 6B:
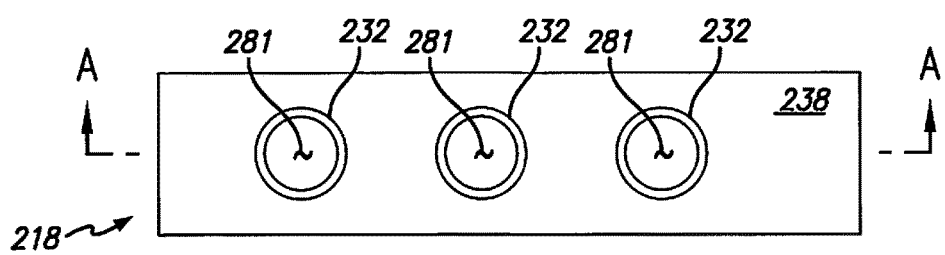
FIG. 6B depicts the flexible circuit prepared for bonding.
Figure 6C:
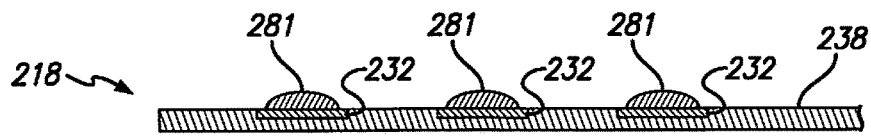
FIG. 6C depicts a cross sectional view of line A-A in FIG. 6B with conductive adhesive.
Figure 6D:
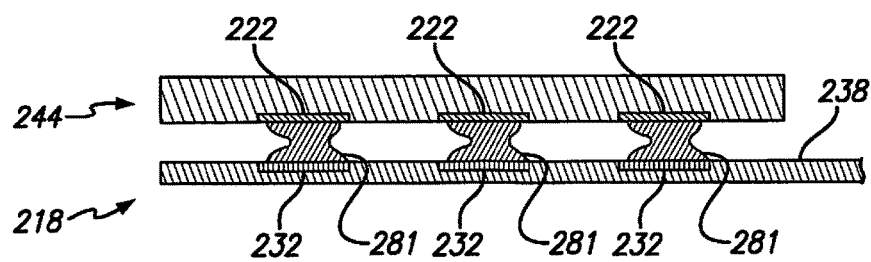
FIG. 6D depicts the bonded assembly.
Figure 6E:
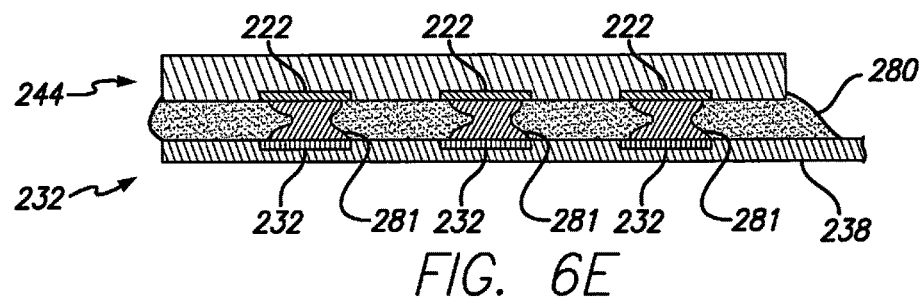
FIG. 6E depicts the bonded assembly with under fill added.
Figure 7A:
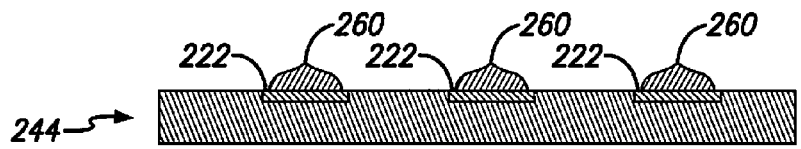
FIG. 7A depicts the beginning of the method of attaching a flexible circuit array to the electronics package where the substrate is prepared for stud bump bonding.
Figure 7B:
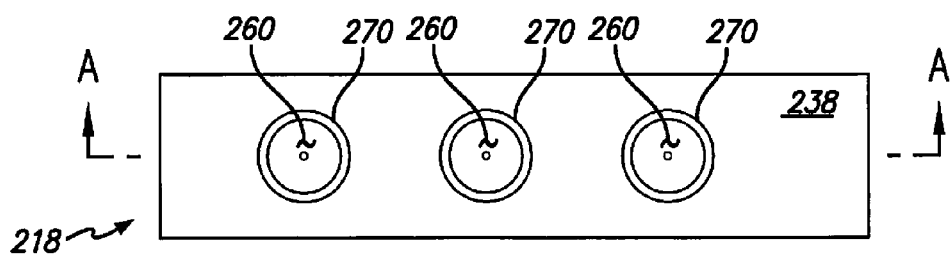
FIG. 7B depicts the flexible circuit prepared for bonding.
Figure 7C:
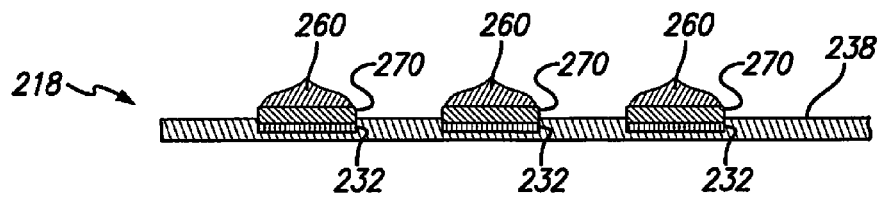
FIG. 7C depicts a cross sectional view of line A-A in FIG. 7B with stud bumps.
Figure 7D:
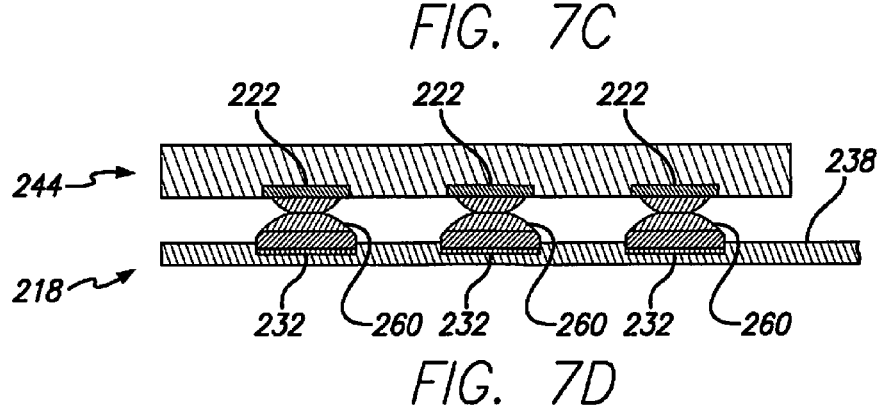
FIG. 7D depicts the bonded assembly.
Figure 7E:
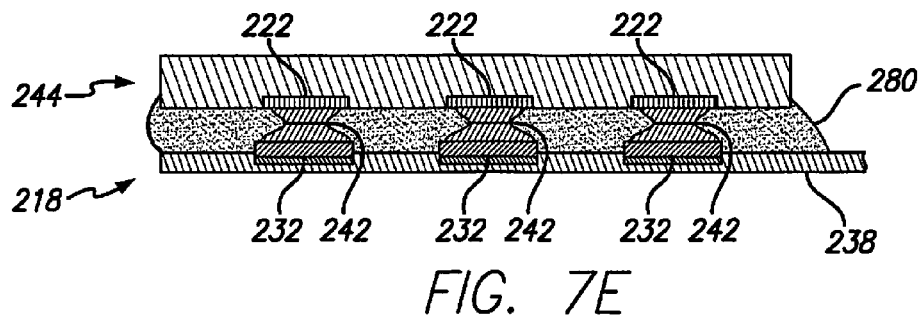
FIG. 7E depicts the bonded assembly with under fill added.
Figure 8A:
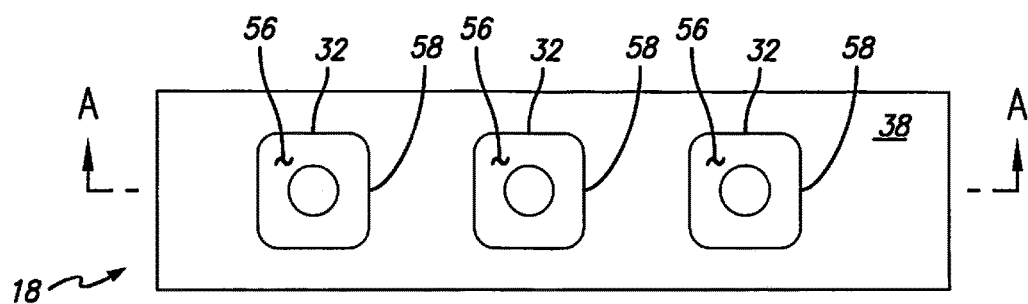
FIG. 8A depicts the beginning of the method of weld staple bonding of a flexible circuit to a hybrid substrate.
Figure 8B:
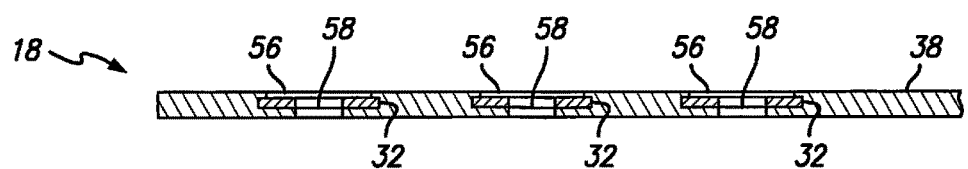
FIG. 8B depicts an A-A cross section of FIG. 8A.
Figure 8C:
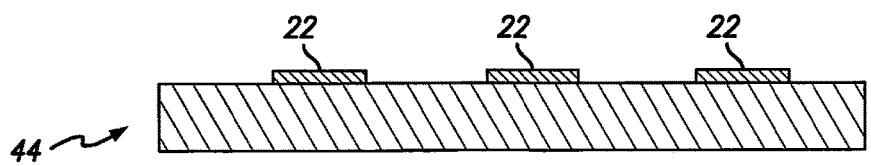
FIG. 8C depicts the hybrid substrate ready for weld staple bonding.
Figure 8D:
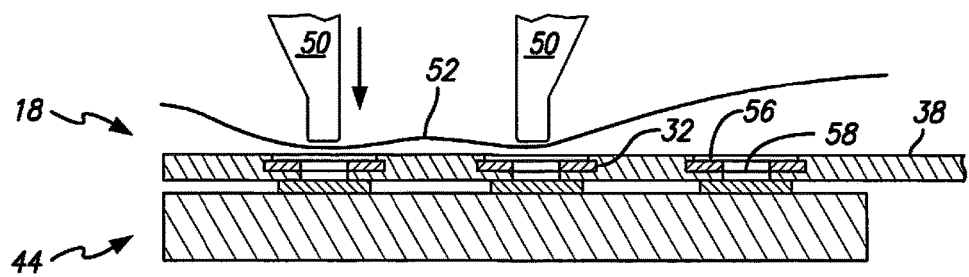
FIG. 8D depicts the hybrid substrate with parts aligned and wire and weld stapler in position.
Figure 8E:
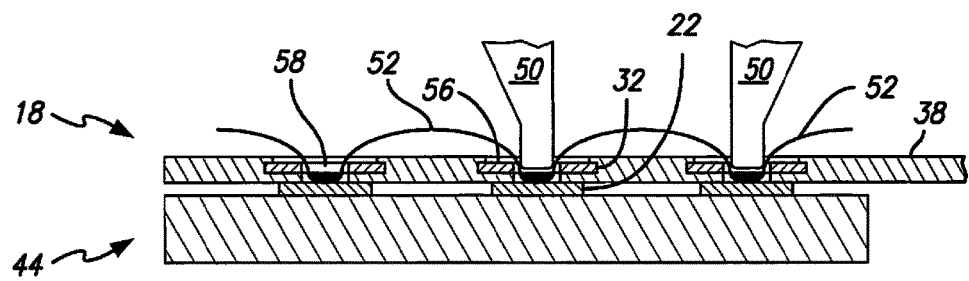
FIG. 8E depicts the parts being weld stapled together.
Figure 8F:
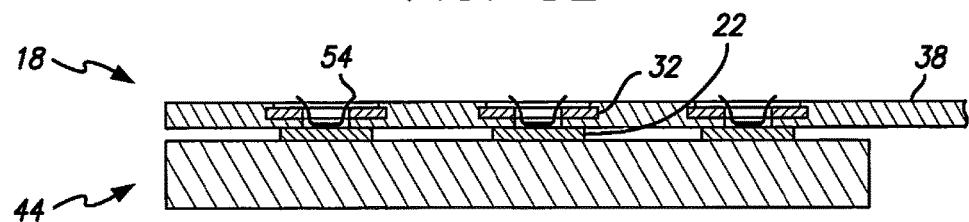
FIG. 8F depicts the finished bonded device.
Figure 9A:
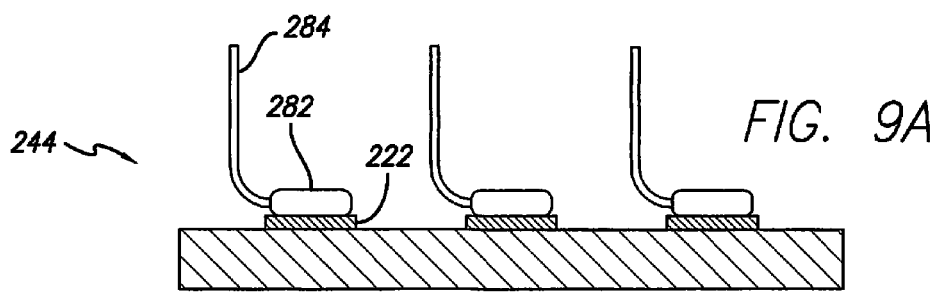
FIG. 9A depicts the beginning of the method of tail-latch interconnect bonding of a flexible circuit to a hybrid substrate.
Figure 9B:
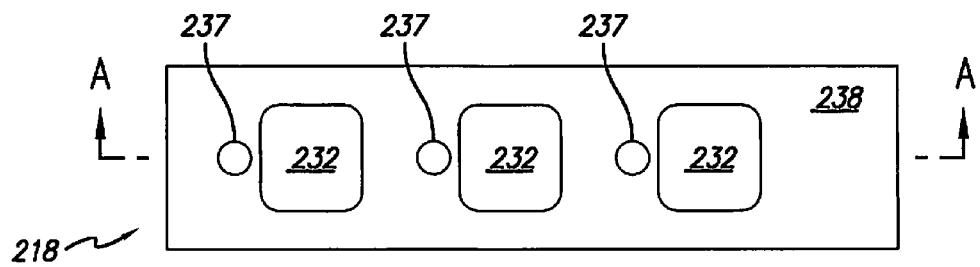
FIG. 9B depicts an A-A cross section of FIG. 9A.
Figure 9C:
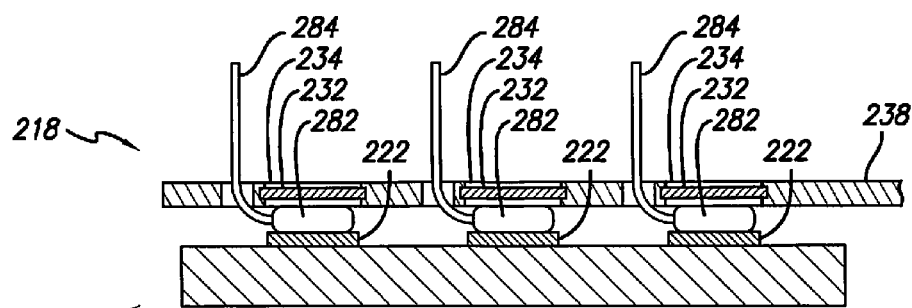
FIG. 9C depicts the flexible circuit in position over the hybrid substrate and the tail extending through the flexible circuit.
Figure 9D:
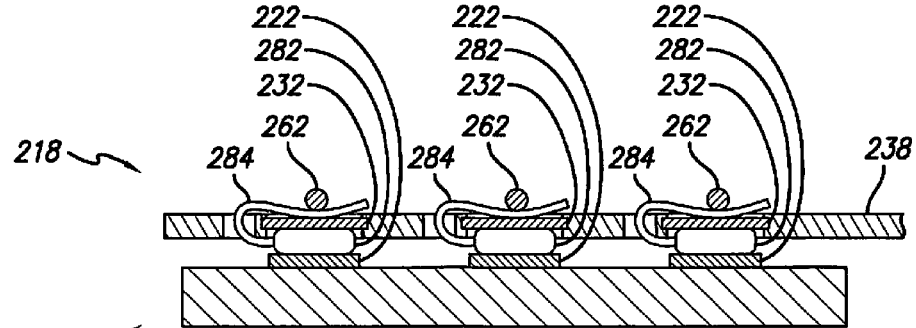
FIG. 9D depicts the bonded unit with the tail welded to the pad on the flexible circuit.
Figure 10A:
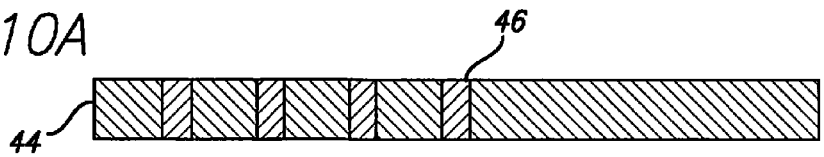
FIG. 10A depicts the first step of formation of an integrated interconnect by vapor deposition.
Figure 10B:
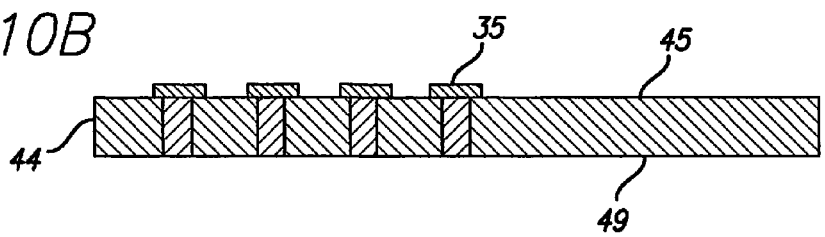
FIG. 10B depicts routing patterned on the hybrid substrate.
Figure 10C:
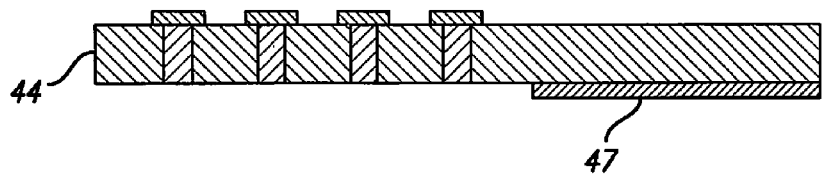
FIG. 10C depicts formation of a release coat on the outside surface of the hybrid substrate.
Figure 10D:
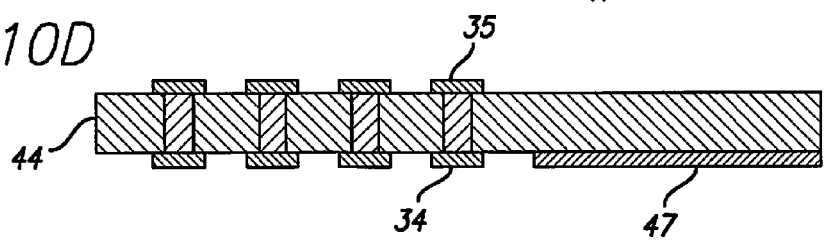
FIG. 10D depicts the formation of traces on the outside of the hybrid substrate.
Figure 10E:
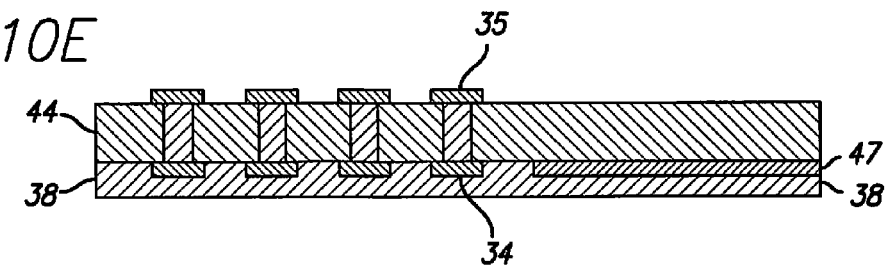
FIG. 10E depicts formation of a flexible insulating substrate.
Figure 10F:
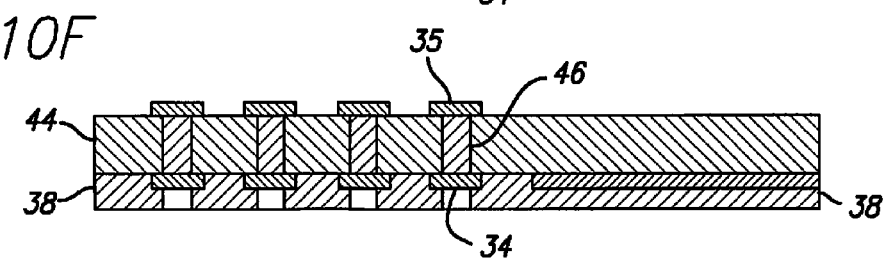
FIG. 10F depicts formation of voids in the flexible insulating substrate.
Figure 10G:
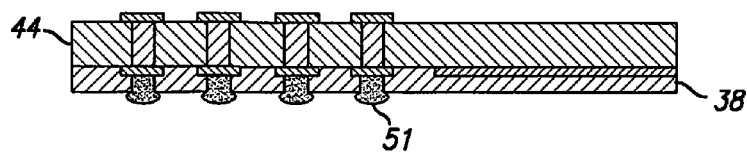
FIG. 10G depicts formation of rivets over the traces.
Figure 10H:
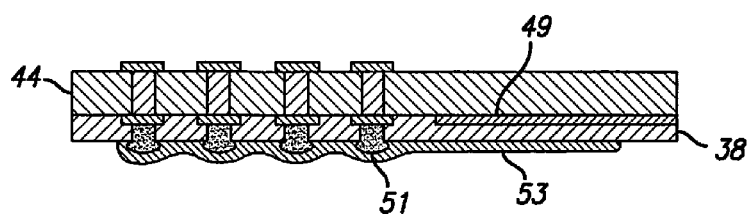
FIG. 10H depicts formation of a metal layer over the rivets.
Figure 10I:
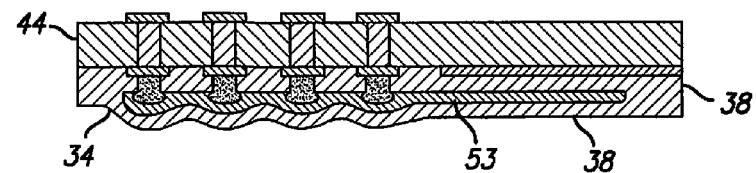
FIG. 10I depicts formation of a flexible insulating substrate over the metal layer.
Figure 10J:
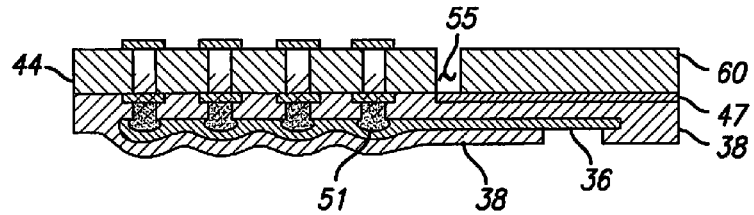
FIG. 10J depicts the hybrid substrate being cut.
Figure 10K:
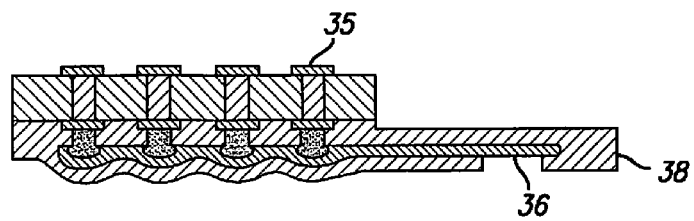
FIG. 10K depicts the flexible circuit attached to the hybrid substrate.
Figure 10L:
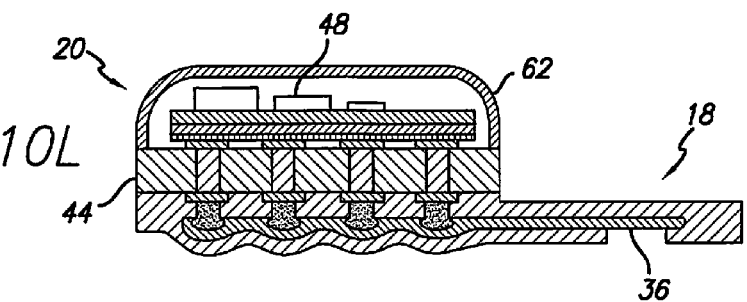
FIG. 10L depicts the completed device.

In FIG. 5, the hermetic electronics control unit 20 is illustrated mounted to flexible circuit 18. In order to assure electrical continuity between the electronics control unit 20 and the flexible circuit 18, the electrical control unit 20 must be intimately bonded to the flexible circuit 18 on the bond pad end 33. A cutaway of the electronics control unit 20 (FIG. 5) illustrates a bonded connection 42. The flexible electrically insulating substrate 38 is very thin and flexible and is able to conform to the curvature of the retina 14 (FIG. 1), when implanted thereon.

Methods of bonding the flexible insulating substrate 18 to the hermetic electronics control unit 20 are discussed next.

Platinum Conductor in Polymer Adhesive

A preferred embodiment of the invention, illustrated in FIG. 6, shows the method of bonding the hybrid substrate 244 to the flexible circuit 218 using electrically conductive adhesive 281, such as a polymer, which may include polystyrene, epoxy, or polyimide, which contains electrically conductive particulate of select biocompatible metal, such as platinum, iridium, titanium, platinum alloys, iridium alloys, or titanium alloys in dust, flake, or powder form.

In FIG. 6, step a, the hybrid substrate 244, which may alternatively be an integrated circuit or electronic array, and the input/output contacts 222 are prepared for bonding by placing conductive adhesive 281 on the input/output contacts 222. The rigid integrated circuit 244 is preferably comprised of a ceramic, such as alumina or silicon. In step b, the flexible circuit 218 is preferably prepared for bonding to the hybrid substrate 244 by placing conductive adhesive 281 on bond pads 232. Alternatively, the adhesive 281 may be coated with an electrically conductive biocompatible metal. The flexible circuit 218 contains the flexible electrically insulating substrate 238, which is preferably comprised of polyimide. The bond pads 232 are preferably comprised of an electrically conductive material that is biocompatible when implanted in living tissue, and are preferably platinum or a platinum alloy, such as platinum-iridium.

FIG. 6, step c illustrates the cross-sectional view A-A of step b. The conductive adhesive 281 is shown in contact with and resting on the bond pads 232. Step d shows the hybrid substrate 244 in position to be bonded to the flexible circuit 218. The conductive adhesive 281 provides an electrical path between the input/output contacts 222 and the bond pads 232. Step c illustrates the completed bonded assembly wherein the flexible circuit 218 is bonded to the hybrid substrate 144, thereby providing a path for electrical signals to pass to the living tissue from the electronics control unit (not illustrated). The assembly has been electrically isolated and hermetically sealed with adhesive underfill 280, which is preferably epoxy.

Studbump Bonding

FIG. 7 illustrates the steps of an alternative embodiment to bond the hybrid substrate 244 to flexible circuit 218 by studbumping the hybrid substrate 244 and flexible electrically insulating substrate 238 prior to bonding the two components together by a combination of heat and/or pressure, such as ultrasonic energy. In step a, the hybrid substrate 244 is prepared for bonding by forming a studbump 260 on the input/output contacts 222. The studbump is formed by known methods and is preferably comprised of an electrically conductive material that is biocompatible when implanted in living tissue if exposed to a saline environment. It is preferably comprised of metal, preferably biocompatible metal, or gold or of gold alloys. If gold is selected, then it must be protected with a water resistant adhesive or underfill 280.

Alternatively, the studbump 260 may be comprised of an insulating material, such as an adhesive or a polymer, which is coated with an electrically conductive coating of a material that is biocompatible and stable when implanted in living tissue, while an electric current is passed through the studbump 260. One such material coating may preferably be platinum or alloys of platinum, such as platinum-iridium, where the coating may be deposited by vapor deposition, such as by ion-beam assisted deposition, or electrochemical means.

FIG. 7, step b presents the flexible circuit 218, which comprises the flexible electrically insulating substrate 238 and bond pads 232. The flexible circuit 218 is prepared for bonding by the plating bond pads 232 with an electrically conductive material that is biocompatible when implanted in living tissue, such as with a coating of platinum or a platinum alloy. Studbumps 260 are then formed on the plated pad 270 by known methods. Step c illustrates cross-section A-A of step b, wherein the flexible circuit 218 is ready to be mated with the hybrid substrate 244.

FIG. 7, step d illustrates the assembly of hybrid substrate 244 flipped and ready to be bonded to flexible circuit 218. Prior to bonding, the studbumps 260 on either side may be flattened by known techniques such as coining. Pressure is applied to urge the mated studbumps 260 together as heat is applied to cause the studbumps to bond by a diffusion or a melting process. The bond may preferably be achieved by thermosonic or thermocompression bonding, yielding a strong, electrically conductive bonded connection 242, as illustrated in step e. An example of a thermosonic bonding method is ultrasound. The bonded assembly is completed by placing an adhesive underfill 280 between the flexible circuit 218 and the hybrid substrate 244, also increasing the strength of the bonded assembly and electrically isolating each bonded connection. The adhesive underfill 280 is preferably epoxy.

Weld Staple Interconnect

FIG. 8 illustrates the steps of a further alternative embodiment to bond the hybrid substrate 44 to flexible circuit 18 by weld staple bonding the substrate 244 and flexible electrically insulating substrate 38 together. In step a, a top view of the flexible circuit 18 is shown. Flexible circuit 18 is comprised of flexible electrically insulating substrate 38, which is preferably polyimide, and bond pads 32 having a through hole 58 therethrough each bond pad 32 and through the top and bottom surfaces of flexible circuit 18. The bond pads 32 are comprised of an electrically conductive and biocompatible material which is stable when implanted in living tissue, and which is preferably platinum or a platinum alloy, such as platinum-iridium.

FIG. 8, step b presents section A-A, which is shown in the illustration of step a. The through holes 58 pass completely through each bond pad 58, preferably in the center of the bond pad 58. They are preferably formed by plasma etching. The bond pads 58 are not covered on the top surface of flexible circuit 18 by flexible electrically insulating substrate 38, thereby creating bond pad voids 56.

FIG. 8, step c shows the side view of hybrid substrate 44 with input/output contacts 22 on one surface thereof. The hybrid substrate 44 is positioned, in step d, to be bonded to the flexible circuit 18 by placing the parts together such that the input/output contacts 22 are aligned with the bond pads 32. Then wire 52, which is preferably a wire, but may equally well be a ribbon or sheet of weldable material, that is also preferably electrically conductive and biocompatible when implanted in living tissue, is attached to input/output contact 22 and bond pad 32 to bond each aligned pair together. The wire 52 is preferably comprised of platinum, or alloys of platinum, such as platinum-iridium. The bond is preferably formed by welding using the parallel gap welder 50, which moves up and down to force the wire 52 into the through hole 58 and into contact with input/output contact 22. This process is repeated for each aligned set of input/output contacts 22 and bond pads 32, as shown in step e.

The weld staple interconnect bonding process is completed, as shown in step f, by cutting the wire 54, leaving each aligned set of input/output contacts 22 and bond pads 32 electrically connected and mechanically bonded together by staple 54.

Tail-Latch Interconnect FIG. 9 illustrates yet another embodiment for attaching the hybrid substrate 244 to a flexible circuit 218 by using a tail-ball 282 component, as shown in step a. The hybrid substrate 244 is preferably comprised of a ceramic material, such as alumina or silicon. In one embodiment, a wire, preferably made of platinum or another electrically conductive, biocompatible material, is fabricated to have a ball on one end, like the preferred tail-ball 282 illustrated in step a. The tail-ball 282 has tail 284 attached thereto, as shown in the side view of step a. The tail-ball 282 is aligned with input/output contact 222 on hybrid substrate 244, in preparation to being bonded to flexible circuit 218, illustrated in step b.

The top view of step b illustrates flexible electrically insulating substrate 238, which is preferably comprised of polyimide, having the through hole 237 passing completely thorough the thickness and aligned with the tail 284. The bond pads 232 are exposed on both the top and bottom surfaces of the flexible circuit 218, by voids 234, enabling electrical contact to be made with input/output contacts 222 of the hybrid substrate 244. The voids are preferably formed by plasma etching.

The side view of FIG. 9, step c, which illustrates section A-A of step b, shows the hybrid substrate 244 in position to be bonded to and aligned with flexible circuit 218. The tails 284 are each placed in through hole 237. Pressure is applied and the tail-balls 282 are placed in intimate contact with bond pads 232 and input/output contacts 222. Step c illustrates that each of the tails 284 is bent to make contact with the bond pads 232. The bonding process is completed by bonding, preferably by welding, each of the tails 284, bond pads 232, tail-balls 282, and input/output contacts 222 together, thus forming a mechanical and electrical bond. Locking wire 262 is an optional addition to assure that physical contact is achieved in the bonded component. The process is completed by underfilling the gap with an electrically insulating and biocompatible material (not illustrated), such as epoxy.

Integrated Interconnect by Vapor Deposition

FIG. 10a through FIG. 10l illustrates a further alternative embodiment to creating a flexible circuit that is electrically and adhesively bonded to a hermetic rigid electronics package. In this approach, the flexible circuit is fabricated directly on the rigid substrate. Step a (FIG. 10a) shows the hybrid substrate 44, which is preferably a ceramic, such as alumina or silicon, having a total thickness of about 0.012 inches, with patterned vias 46 therethrough. The vias 46 are preferably comprised of frit containing platinum.

In step b (FIG. 10b), the routing 35 is patterned on one side of the hybrid substrate 44 by known techniques, such as photolithography or masked deposition. It is equally possible to form routing 35 on both sides of the substrate 44. The hybrid substrate 44 has an inside surface 45 and an outside surface 49. The routing 35 will carry electrical signals from the integrated circuit, that is to be added, to the vias 46, and ultimately will stimulate the retina (not illustrated). The routing 35 is patterned by know processes, such as by masking during deposition or by post-deposition photolithography. The routing 35 is comprised of a biocompatible, electrically conductive, patternable material, such at platinum.

Step c (FIG. 10c) illustrates formation of the release coat 47 on the outside surface 49 of the hybrid substrate 44. The release coat 47 is deposited by known techniques, such as physical vapor deposition. The release coat 47 is removable by know processes such as etching. It is preferably comprised of an etchable material, such as aluminum.

Step d (FIG. 10d) illustrates the formation of the traces 34 on the outside surface 49 of the hybrid substrate 44. The traces 34 are deposited by a known process, such as physical vapor deposition or ion-beam assisted deposition. They may be patterned by a known process, such as by masking during deposition or by post-deposition photolithography. The traces 34 are comprised of an electrically conductive, biocompatible material, such as platinum, platinum alloys, such as platinum-iridium, or titanium-platinum. The traces 34 conduct electrical signals along the flexible circuit 18 and to the stimulating electrode array 10, which were previously discussed and are illustrated in FIG. 4.

Step e (FIG. 10e) illustrates formation of the flexible electrically insulating substrate 38 by known techniques, preferably liquid precursor spinning. The flexible electrically insulating substrate 38 is preferably comprised of polyimide. The flexible electrically insulating substrate electrically insulates the traces 34. It is also biocompatible when implanted in living tissue. The coating is about 5 um thick. The liquid precursor is spun coated over the traces 34 and the entire outside surface 49 of the hybrid substrate 44, thereby forming the flexible electrically insulating substrate 38. The spun coating is cured by known techniques.

Step f (FIG. 10f) illustrates the formation of voids in the flexible electrically insulating substrate 38 thereby revealing the traces 34. The flexible electrically insulating substrate is preferably patterned by known techniques, such as photolithography with etching.

Step g (FIG. 10g) illustrates the rivets 51 having been formed over and in intimate contact with traces 34. The rivets 51 are formed by known processes, and are preferably formed by electrochemical deposition of a biocompatible, electrically conductive material, such as platinum or platinum alloys, such as platinum-iridium.

Step h (FIG. 10h) illustrates formation of the metal layer 53 over the rivets 51 in a controlled pattern, preferably by photolithographic methods, on the outside surface 49. The rivets 51 and the metal layer 53 are in intimate electrical contact. The metal layer 53 may be deposited by known techniques, such as physical vapor deposition, over the entire surface followed by photolithographic patterning, or it may be deposited by masked deposition. The metal layer 53 is formed of an electrically conductive, biocompatible material, which in a preferred embodiment is platinum. The patterned metal layer 53 forms traces 34 and electrodes 36, which conduct electrical signals from the electronics control unit 20 and the electrodes 36 (see FIGS. 4 and 5).

Step i (FIG. 10*i*) illustrates the flexible electrically insulating substrate 38 applied over the outside surface 49 of the rigid substrate 44, as in step e. The flexible electrically insulating substrate 38 covers the rivets 51 and the metal layer 53.

Step j (FIG. 10*j*) illustrates the hybrid substrate 44 having been cut by known means, preferably by a laser or, in an alternative embodiment, by a diamond wheel, thereby creating cut 55. The portion of hybrid substrate 44 that will be removed is called the carrier 60.

The flexible electrically insulating substrate 38 is patterned by known methods, such as photolithographic patterning, or it may be deposited by masked deposition, to yield voids that define the electrodes 36. The electrodes 36 transmit electrical signals directly to the retina of the implanted eye (see FIG. 4).

Step k (FIG. 10*j*) illustrates flexible circuit 18 attached to the hybrid substrate 44. The carrier 60 is removed by utilizing release coat 47. In a preferred embodiment, release coat 47 is etched by known means to release carrier 60, leaving behind flexible circuit 18.

Step l (FIG. 10*l*) illustrates the implantable electronic device of a flexible circuit 18 and an intimately bonded hermetic electronics control unit 20. The electronics control unit 20, which contains the microelectronics assembly 48, is hermetically sealed with header 62 bonded to rigid circuit substrate 44. The header 62 is comprised of a material that is biocompatible when implanted in living tissue and that is capable of being hermetically sealed to protect the integrated circuit electronics from the environment.

FIG. 11 illustrates an electronics control unit 320 attached to flexible electrically insulating substrate 338, which is preferably comprised of polyimide, by bonded connections 342. The electronics control unit 320 is preferably a hermetically sealed integrated circuit, although in an alternative embodiment it may be a hermetically sealed hybrid assembly. Bonded connections 342 are preferably conductive adhesive, although they may alternatively be solder bumps. The bond area is underfilled with an adhesive 380. Rigid stimulating electrode array 310 is attached to the flexible electrically insulating substrate 338 by bonded connections 342.

FIG. 12 illustrates an electronics control unit 320 attached to rigid stimulating electrode array 310 by bonded connections 342. The bond area is then underfilled with an adhesive 380, preferably epoxy. Bonded connections 342 are preferably conductive adhesive, although they may alternatively be solder bumps.

Figure 13A:
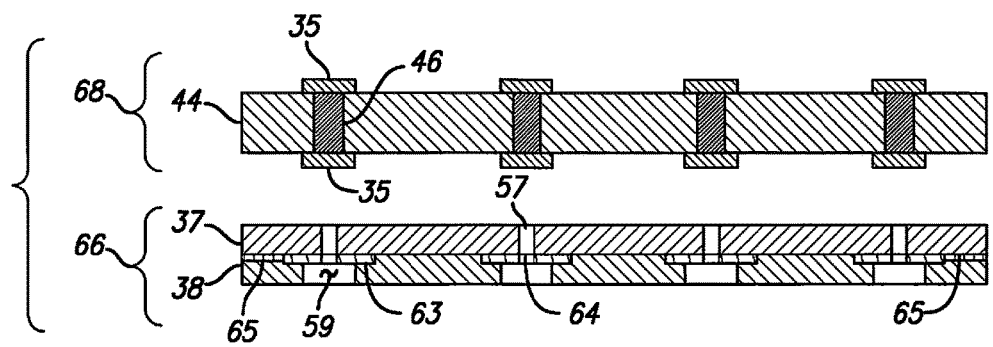
FIG. 13 is a cross-sectional view of a bonded assembly in stepwise fashion.
Figure 13B:
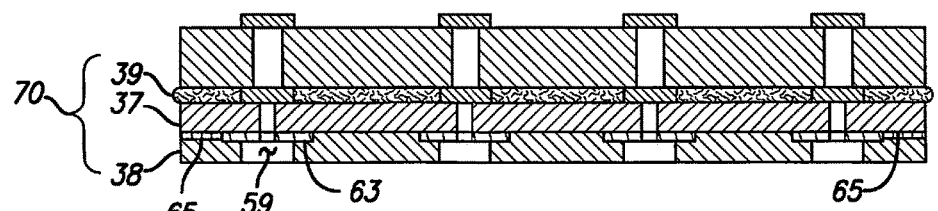
Figure 13C:
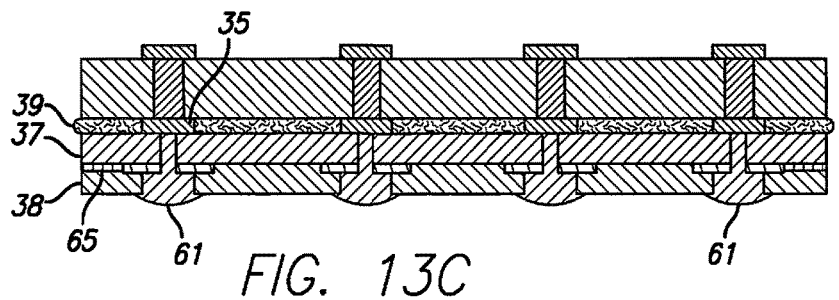

The bonding steps are illustrated in FIG. 13 for a flex circuit assembly that is bonded with rivets 61 that are created in situ by a deposition process, preferably by electroplating. The rivets 61 are rivet-shaped electrical connections. The substrate 68 is shown generally in FIG. 13. It is comprised of the hybrid substrate 44, which is preferably a ceramic, such as alumina or silicon. The silicon would preferably be coated with a biocompatible material to achieve biocompatibility of the silicon, which is well known to slowly dissolve when implanted in living tissue.

The hybrid substrate 44 preferably contains vias 46 that pass through the thickness of the hybrid substrate 44, see FIG. 13, step (a). Vias 46 are not required to enable this invention, and are not present in alternative embodiments. It is preferred that the hybrid substrate 44 be rigid, although alternative embodiments utilize a non-rigid substrate. The vias 46 are integral with electrically conductive routing 35 that has been placed on the surface of the hybrid substrate 44 by known techniques. The routing is preferably comprised of a stable biocompatible material, such as platinum, a platinum alloy, or gold, most preferably platinum.

A flexible electrically insulating substrate 38 is preferably comprised of two layers of an electrically insulating material, such as a polymer. Known preferred polymer materials are polyimide or Parylene. Parylene refers to polyparaxylylene, a known polymer that has excellent implant characteristics. For example, Parylene, manufactured by Specialty Coating Systems (SCS), a division of Cookson Electronic Equipment Group, located in Indianapolis, Ind., is a preferred material. Parylene is available in various forms, such as Parylene C, Parylene D, and Parylene N, each having different properties. The preferred form is Parylene C.

The flexible electrically insulating substrate layers 38 are preferably of approximately equal thicknesses, as illustrated in FIG. 13, step (a). A trace 65 is also illustrated in FIG. 13, step (a), where trace 65 may be at least one, but preferably more than one, trace 65 that is electrically conductive. The traces 65 are integrally bonded to bond pads 63. The bond pads 63 each have a bond pad hole 64 therethrough, which is in approximate alignment with first hole 57 in first electrically insulating substrate 37 and second hole 59 in the second flexible electrically insulating substrates 38, such that there is a hole, with centers approximately aligned, through the thickness of the flexible assembly 66.

The flexible assembly 66 is placed next to the hybrid substrate in preparation for bonding, FIG. 13, step (b). The flexible assembly aligned holes that are formed by first substrate holes 57, bond pad holes 64, and second substrate holes 59 are aligned with the routing 35. In a preferred embodiment, there is at least one via 46, although no via 46 is required. In a preferred embodiment, an adhesive layer 39 is applied to adhesively bond the assembly together. The adhesive is preferably epoxy, silicone, or polyimide. In alternative embodiments, the assembly is not adhesively bonded.

As illustrated in FIG. 13, step (c), a rivet 61 is formed in each flexible substrate hole to bond the assembly together. The rivets 61 are preferably formed by a deposition process, most preferably electroplating. The rivets 61 are comprised of a biocompatible, electrically conductive material, preferably platinum, although alternative embodiments may utilize platinum alloys (e.g. platinum-iridium or platinum-rhodium), iridium, gold, palladium, or palladium alloys. It is most preferred that rivet 61 be comprised of electroplated platinum, called "plated platinum" herein.

Figure 14:
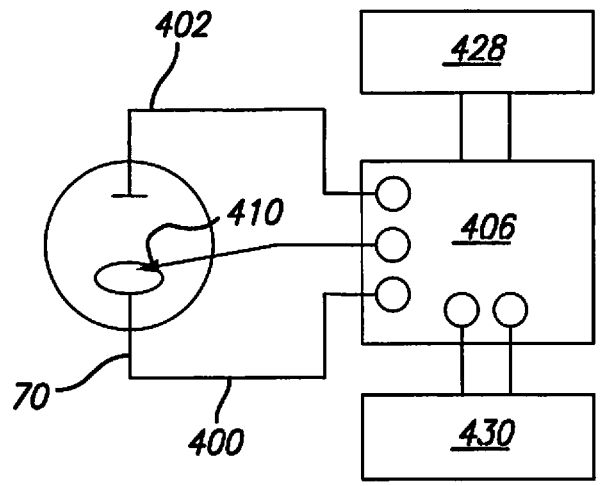
FIG. 14 is an electroplating equipment schema.
Figure 15:
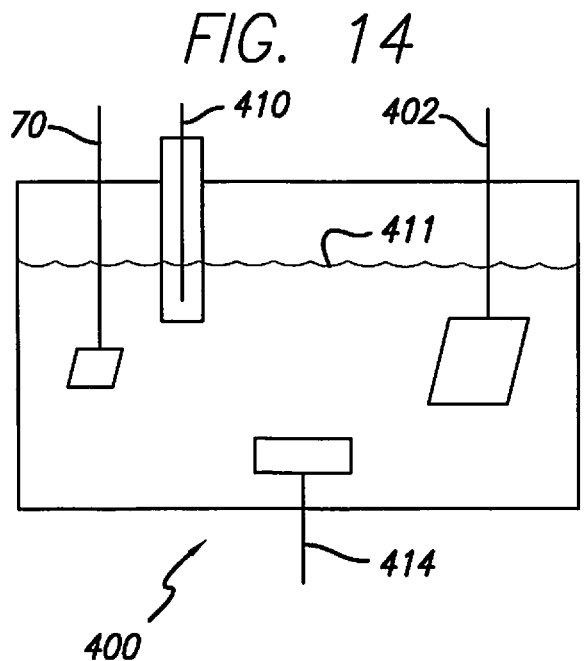
FIG. 15 is a three-electrode electroplating cell schema.

Referring to FIGS. 14 and 15, a method to produce plated platinum according to the present invention is described comprising connecting a common electrode 402, the anode, and a bonded assembly 70, the cathode, to a voltage to current converter 406 with a wave form generator 430 and monitor 428, preferably an oscilloscope. The common electrode 402, bonded assembly 70, a reference electrode 410, for use as a reference in controlling the power source, which is comprised of a voltage to current converter 406 and a waveform generator 430, and an electroplating solution are placed in a electroplating cell 400 having a means for mixing 414 the electroplating solution. Power may be supplied to the electrodes with constant voltage, constant current, pulsed voltage, scanned voltage or pulsed current to drive the electroplating process. The waveform generator 430 and voltage to current converter 406 is set such that the rate of deposition will cause the platinum to deposit as plated platinum of the present invention, the rate being greater than the deposition rate necessary to form shiny platinum and less than the deposition rate necessary to form platinum black.

Because no impurities or other additives, such as lead, which is a neurotoxin and cannot be used in an implantable device, need to be introduced during the plating process to produce plated platinum of the present invention, the plated material can be pure platinum. Alternatively, other materials can be introduced during the plating process, if so desired, but these materials are not necessary to the formation of plated platinum of the present invention.

Referring to FIGS. 14 and 15, the electroplating cell 400, is preferably a 50 ml to 150 ml four neck glass flask or beaker, the common electrode 402, or anode, is preferably a large surface area platinum wire or platinum sheet, the reference electrode 410 is preferably a Ag/AgCl electrode (silver, silver chloride electrode), the bonded assembly 70, or cathode, can be any suitable material depending on the application and can be readily chosen by one skilled in the art. Preferable examples of the bonded assembly 70 include, but are not limited to, platinum, iridium, rhodium, gold, tantalum, titanium or niobium, preferably platinum.

The means for mixing 414 is preferably a magnetic stirrer (FIG. 15). The plating solution is preferably 3 to 30 millimoles ammonium hexachloroplatinate in 0.4 moles of disodium hydrogen phosphate, but may be derived from any chloroplatinic acid or bromoplatinic acid or other electroplating solution. The preferable plating temperature is approximately 24° C.-26° C.

Figure 16:
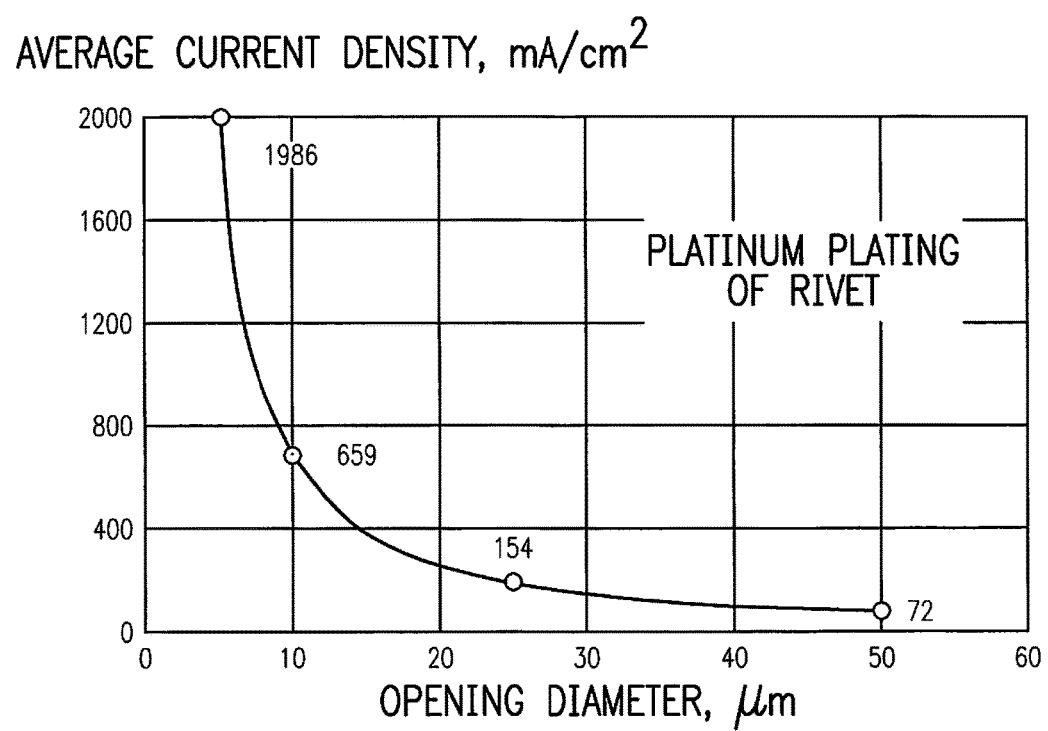
FIG. 16 is a plot of showing the plating current density decrease with hole size.

The electroplating system for pulsed current control is shown in FIGS. 14 and 15. While constant voltage, constant current, pulsed voltage or pulsed current can be used to control the electroplating process, pulsed current control of the plating process is preferable for plating rivets 61, which have a height that approximates their diameter. The preferable current range to produce plated platinum of the present invention, which varies from about 50 to 2000 mA/cm$^2$, is dependent on the hole dimensions, FIG. 16, where the response voltage ranges from about −0.45 volts to −0.85 volts. Applying power in this range with the above solution yields a plating rate in the range of about 0.05 urn per minute to 1.0 um per minute, the preferred range for the plating rate of plated platinum of the present invention. The average current density may be determined by the equation $y=19572x^{-1.46}$, where y is the average current density in mA/cm$^2$ and x is the hole diameter in microns. Pulsed current control also allows an array of rivets to be plated simultaneously achieving uniform rivet properties.

As plating conditions, including but not limited to the plating solution, surface area of the electrodes, pH, platinum concentration and the presence of additives, are changed the optimal control parameters will change according to basic electroplating principles. Plated platinum of the present invention will be formed so long as the rate of deposition of the platinum particles is slower than that for the formation of platinum gray and faster than that for the formation of shiny platinum.

It has been found that because of the physical strength of plated platinum of the present invention, it is possible to plate rivets of thickness greater than 30 microns. It is very difficult to plate shiny platinum in layers greater than approximately two microns because the internal stresses of the dense platinum layer cause the plated layer to peel off.

Plated platinum of the present invention can be distinguished from two other forms of electroplated platinum, specifically, platinum gray and platinum black, based on the adhesive strength of a thin film coating of these materials. Adhesive strength of thin film coatings of platinum gray and platinum black on electrically conductive articles has been measured on a Micro-Scratch Tester (CSEM Instruments, Switzerland). A 400 micron micro-scratch is formed by drawing a diamond tip, having a 10 micron spherical radius, across the coating under a load that is increased in a controlled manner from 1 millinewton to 100 millinewtons. At the "critical load", the coating fails. Using this test, it is found that plated platinum of the present invention fails at an estimated critical load of about 70 millinewtons, platinum gray fails at a measured critical load of 61 millinewtons, while platinum black fails at a measured critical load of less than about 35 millinewtons.

Likewise, the several forms of platinum are distinguished by their hardness. For example, the microhardness, as measured with a Vickers indenter, is estimated to be about 30 for plated platinum of the present invention, while it is estimated to be less than one for platinum black, it is measured to be 17 for platinum gray, and is estimated to be about 34 for shiny platinum, and it is reported to be 40 for platinum foil, and 100 for cold worked platinum (Materials Engineering, Materials Selector 1990, Penton Publishing, 1989, p 122). On a hybrid substrate 44, a thin-layer routing 35, preferably platinum, is sputtered and then covered with about 6 µm thick flexible assembly 66, preferably polyimide, with holes in the range from 5 µm to 50 µm. On each sample, preferably about 100 to 700 or more such holes are exposed for plating of rivets 61, see FIG. 17a.

SEM micrographs record the surface appearance before plating. The surface is chemically and electrochemically cleaned before plating.

The electrodes in the test cell are arranged, so that the bonded assembly 70 (cathode) is physically parallel with the common electrode 402 (anode). The reference electrode 410 is positioned beside the bonded assembly 70. The plating solution is added to electroplating solution level 411. The solution is comprised of about 18 millimoles ammonium hexachloroplatinate in about 0.4 moles phosphate buffer solution. The amount of solution used depends on the number of rivets 61 to be plated. The means for mixing 414, preferably a magnetic stirrer, is activated.

A voltage waveform is generated, preferably with a 1 msec pulse width as a 500 Hz square wave, which is converted to a current signal through a voltage to current converter 406.

The pulse current is applied to the plating electrode versus anode. The electrode voltage versus Ag/AgCl reference electrode is monitored using an oscilloscope (Tektronix TDS220 Oscilloscope). The current amplitude is adjusted so that the cathodic peak voltage reaches about −0.6 V versus the Ag/AgCl reference electrode 410. During plating, the electrode voltage tends to decrease with plating time. The current amplitude is frequently adjusted so that the electrode voltage is kept within −0.5 to −0.7 V range versus Ag/AgCl reference electrode 410. When the specified plating time is reached, the current is eliminated. The cathode is rinsed in deionized water thoroughly. Typical plating time is in the range of about 5 to 60 minutes, preferably 15 to 25 minutes.

The plated surface is examined under an optical microscope. Optical photomicrographs are taken at both low and high magnifications to record the image of the surface. The plated samples are profiled with a surface profilometer to measure the dimensions of the plated rivet. The total plated rivet has a total height of about 8 to 16 µm.

After plating, the pulsing current amplitudes are averaged for the total plating time and recorded. It has been demonstrated that the current density increases exponentially with sample hole decrease. The smaller the sample holes, the higher the current density required (see FIG. 16).

Figure 17A:
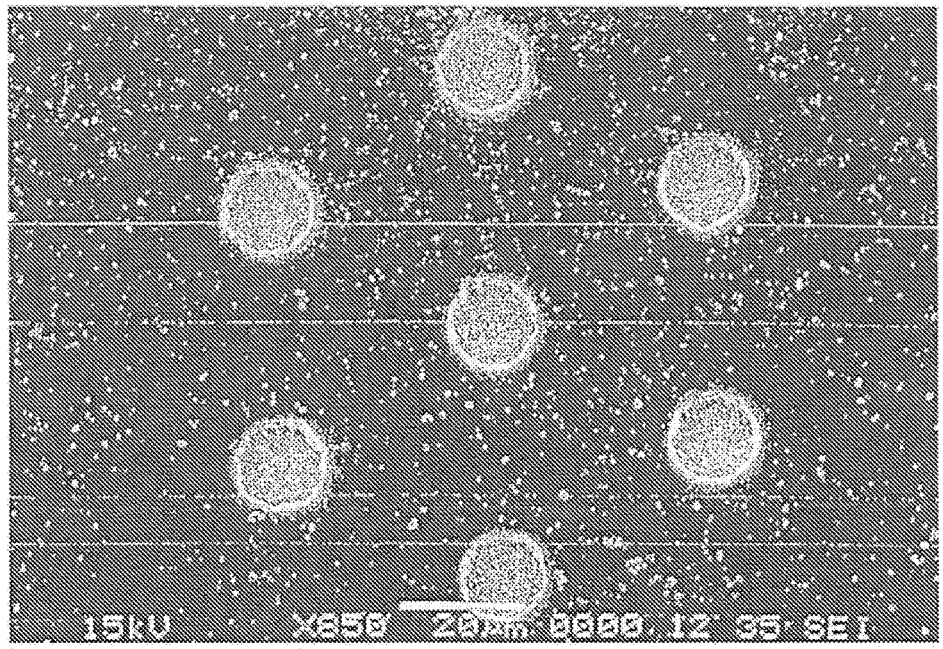
FIG. 17a is a scanning electron micrograph of a polyimide surface before plating magnified 850 times.
Figure 17B:
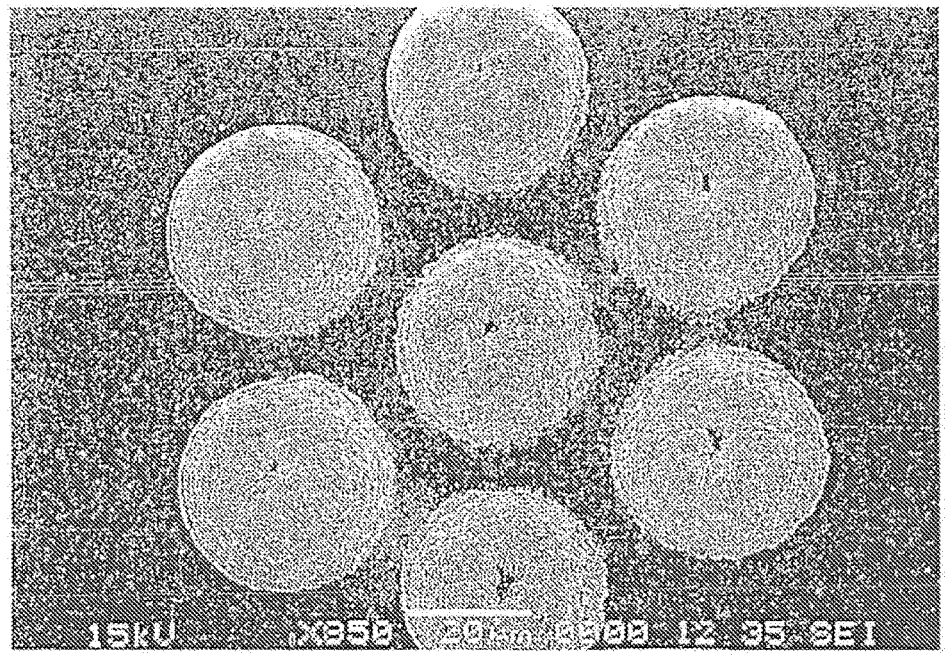
FIG. 17b is a scanning electron micrograph of electrochemically deposited rivets magnified 850 times

An illustrative example of a plated platinum rivet according to the present invention are micrographs produced on a Scanning Electron Microscope (SEM) at 850.times. taken by a JEOL JSM5910 microscope, FIGS. 17a and 17b.

Furthermore, it has been found that because of the physical strength of plated platinum of the present invention, it is possible to plate rivets 61 of thickness greater than 16 um. It is very difficult to plate shiny platinum in layers greater than approximately 1 to 5 µm because the internal stress of the dense platinum layer which will cause plated layer to peel off.

The following example is illustrative of electroplating platinum as a rivet 61, according to the present invention.

EXAMPLE

A flexible electrically insulating substrate comprised of a first substrate 37 and a second substrate 38 of polyimide having a total thickness of 6 urn. It had 700 first substrate holes 57, an equal number of matching bond pad holes 64, and an equal number of matching second substrate holes 59, all in alignment so as to create a continuous hole through flexible assembly 66 that terminates on routing 35, arranged in 100 groups of seven on about 40 um centers, FIG. 4a. The hybrid substrate 44 was alumina and the routing 35 was platinum. The bond pad 63 was platinum.

The assembly was cleaned by rinsing three times in 10% HCl. It was further prepared by bubbling for 10 seconds at +/−5V at 1 Hz in phosphate buffered saline Finally, it was rinsed in deionized water.

The electroplating set up according to FIGS. 14 and 15 was comprised of an electroplating cell 400 that was a 100 ml beaker with an electroplating solution level 411 at about the 75 ml level. The solution was 18 millimoles of ammonium hexachloroplatinate in 0.4 moles phosphate buffer solution.

The means for mixing 414 was a magnetic stirrer, which was activated. The voltage waveform of 1 msec pulse width as a square wave, was generated by an HP 33120A waveform generator, which is converted to current signal through a voltage to current converter 406. The pulse current was 1 msec in pulse width at 500 Hz square wave.

The pulse current was applied on the plating electrode bonded assembly 70 versus common electrode 402. The electrode voltage versus Ag/AgCl reference electrode 410 was monitored using as a monitor 428 a Tektronix model TDS220 oscilloscope. The current amplitude was increased so that the bonded assembly 70 (cathode) peak voltage reached −0.6 V versus the Ag/AgCl reference electrode 410. During plating, the electrode voltage decreased with plating time.

The average current density was 660 mA/cm$^2$, which generated response voltages of −0.5 to −0.7 volts, where the voltage was controlled by the current. A 1 msec pulse width square wave was generated by an HP 33120A Arbitrary Waveform Generator. The pulse was converted to a current signal through a voltage to current converter 406. The pulse current was typically about 1 msec in pulse width as a 500 Hz square wave. The resulting plated platinum rivet 61 was about 32 µm diameter on the button end and about 15 µm tall, with about 9 µm of the height extending above the polyimide substrate. The plated platinum rivet was dense, strong, and electrically conductive.

Scanning Electron Microscope (SEM)/energy dispersive analysis (EDAX™) analysis were performed on the rivets 61. SEM micrographs of the plated surface were taken showing its as-plated surface, FIG. 17b. Energy dispersed analysis demonstrated that the rivet 61 was pure platinum, with no detectable oxygen.

The above described is the preferred embodiment of the current invention, however the platinum electrodeposition described in U.S. Pat. No. 6,974,533 and incorporated herein by reference, is also effective for forming electrochemically deposited rivets.

The rivet 61 (FIG. 13) forms an electrically conductive bond with the routing 35 and with the bond pad 63. It is obvious that the bonded assembly may be stacked with other bonded assemblies forming multiple stacked assemblies with increased stacking density.

Accordingly, what has been shown is an improved flexible circuit with an electronics control unit attached thereto, which is suitable for implantation in living tissue and to transmit electrical impulses to the living tissue. Obviously, many modifications and variations of the present invention are possible in light of the above teachings. It is therefore to be understood that, within the scope of the appended claims, the invention may be practiced other than as specifically described.

The invention claimed is:
1. An implantable electronic device comprising:
a hermetic electronics control unit including a bond pad,
a first thin film flexible electrically insulating substrate;
an electrically conducting metal layer deposited on the first insulating layer;
a second thin film flexible electrically insulating substrate deposited on the electrically conducting metal layer;
at least one of the first flexible electrically insulating substrate or the second flexible electrically insulating substrate defining a hole that expose the electrically conducting metal layer forming a contact; and
an electrically conductive studbump for bonding the bond pad to the contact.
2. The implantable electronic device according to claim 1, wherein the stud bump is comprised of platinum or a platinum alloy.
3. The implantable electronic device according to claim 1, wherein the stud bump is comprised of gold or a gold alloy.
4. The implantable electronic device according to claim 1, further comprising under fill surrounding the studbump.
5. The implantable electronic device according to claim 1, further comprising plating to thicken the bond pad.
6. The implantable electronic device according to claim 1, further comprising plating to thicken the contact.
7. The implantable electronic device according to claim 1, wherein the each half of the studbump is flattened by coining.
8. The implantable electronic device according to claim 1, wherein the studbump is bonded by ultrasonic energy.
9. The implantable electronic device according to claim 1, wherein the studbump is bonded by diffusion.
10. The implantable electronic device according to claim 1, wherein the studbump is bonded by thermosonic bonding.
11. The implantable electronic device according to claim 1, wherein the studbump is bonded by thermocompression bonding.

* * * * *